United States Patent [19]

Trumbull et al.

[11] 3,998,217
[45] Dec. 21, 1976

[54] SURGICAL RETRACTOR DEVICE

[75] Inventors: William Ernest Trumbull, Los Angeles; James Joseph Cogley, Santa Monica, both of Calif.

[73] Assignees: William E. Trumbull; James J. Cogley, both of Santa Monica, Calif.; part interest to each

[22] Filed: Jan. 13, 1975

[21] Appl. No.: 540,323

[52] U.S. Cl. ............................................. 128/20
[51] Int. Cl.$^2$ ................................... A61B 17/02
[58] Field of Search .................. 128/20, 346, 87 R

[56] References Cited

UNITED STATES PATENTS

| | | | |
|---|---|---|---|
| 590,625 | 9/1897 | Paquette | 128/85 |
| 1,157,202 | 10/1915 | Bates et al. | 128/20 |
| 2,623,517 | 12/1952 | Barlow et al. | 128/20 |
| 3,070,088 | 12/1962 | Brahos | 128/20 |
| 3,384,077 | 5/1968 | Gauthier | 128/20 |
| 3,394,700 | 7/1968 | Yamamoto | 128/20 |
| 3,710,783 | 1/1973 | Jascalevich | 128/20 |

*Primary Examiner*—Robert W. Michell
*Assistant Examiner*—Henry S. Layton
*Attorney, Agent, or Firm*—Henry M. Bissell

[57] ABSTRACT

An improved surgical retractor device comprises a preferably generally flat, ring-shaped retractor frame with an open central working portion, a plurality of preferably generally flat surgical retractors with depending surgical opening-retracting ends, and connector means comprising spaced studs and mating holes on the frame and retractors to releasably secure the retractors in place without danger of pivoting of the retractors in use. Each retractor can be put in place and locked on the frame with one hand, so that its depending end extends into the open central portion of the frame for effective use. Each retractor can also be adjusted in position relative to the frame with one hand while the frame is in use. The device is simple, inexpensive, foolproof, durable and very easily used and sterilized. It contains no moving parts and cannot be easily damaged.

9 Claims, 8 Drawing Figures

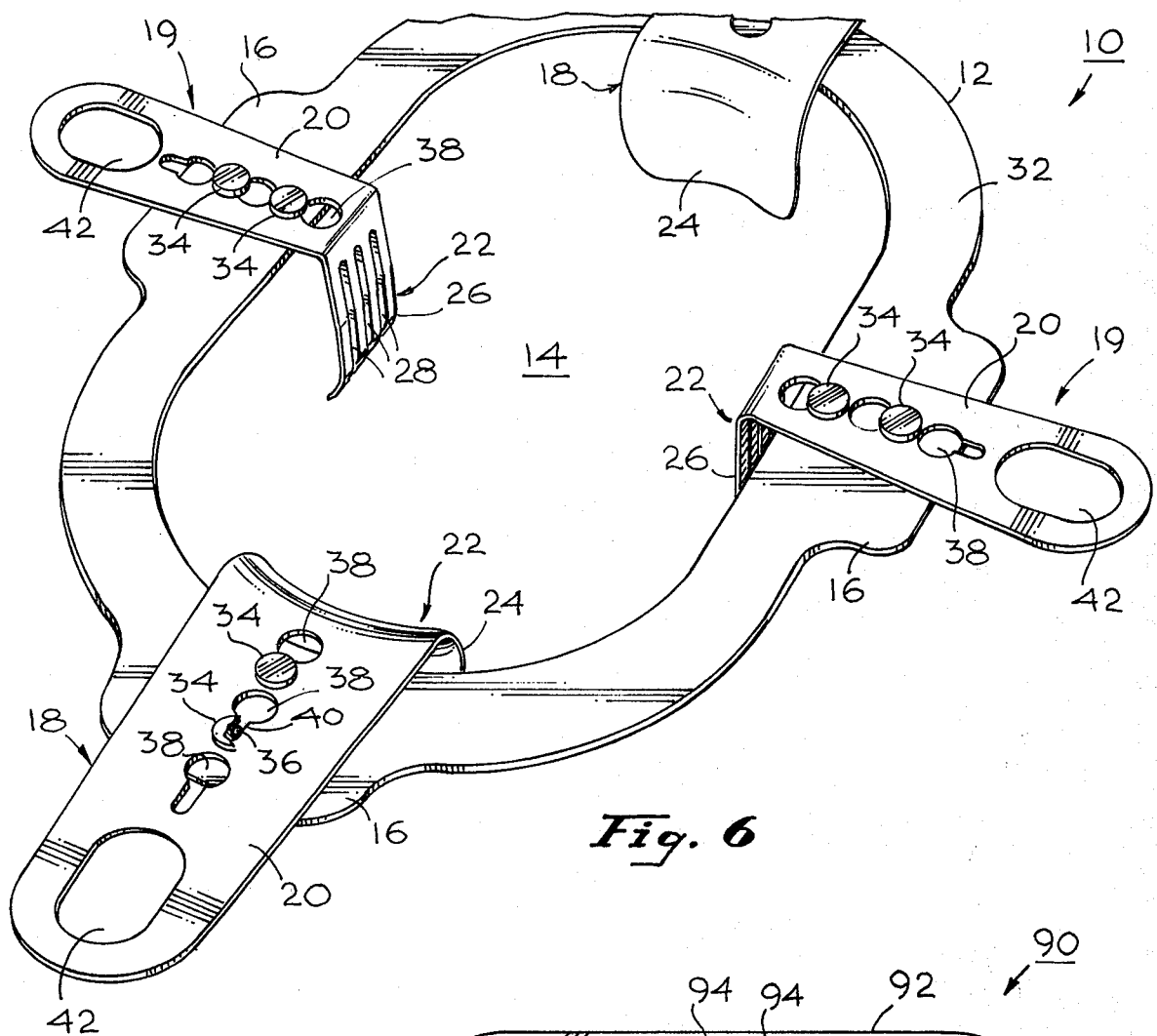
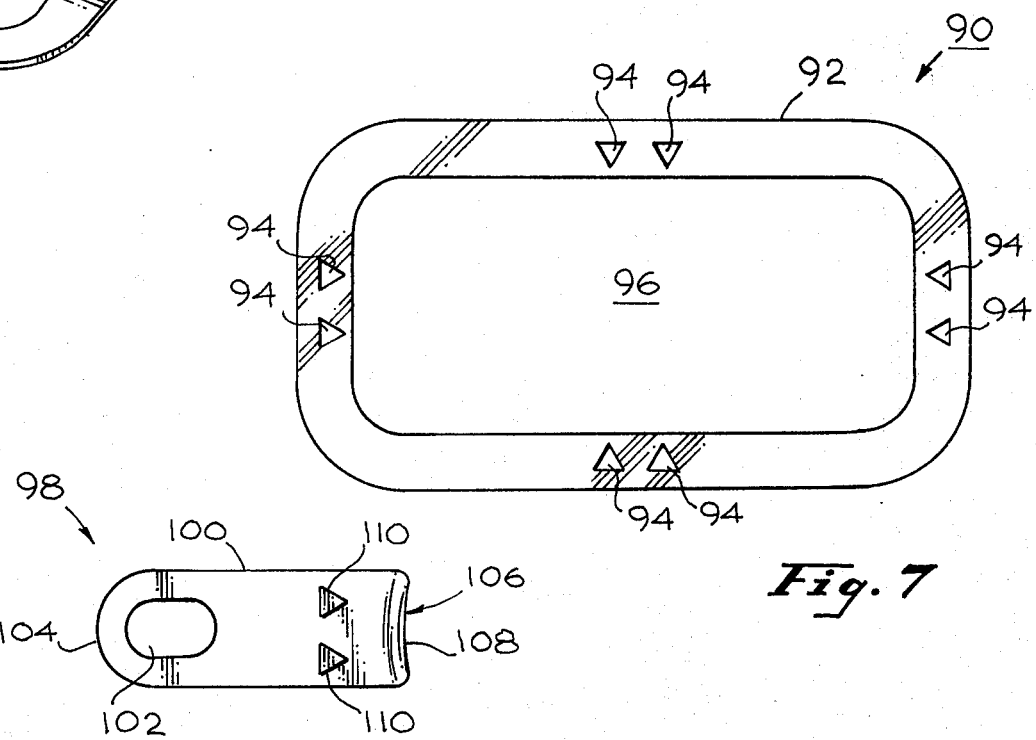
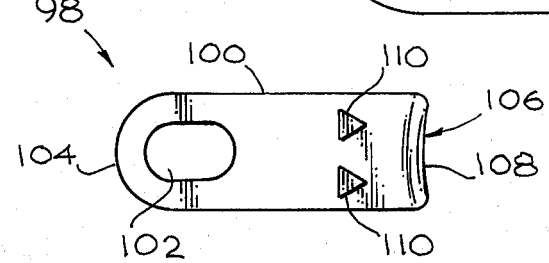

SURGICAL RETRACTOR DEVICE

BACKGROUND OF THE INVENTION

1. Field of the Invention

The present invention generally relates to surgical devices and more particularly to adjustable surgical retractor devices.

2. Description of the Prior Art

Retractors are useful in keeping the operating field open and viewable during a surgical operation. Various types of surgical retractor frames with attached retractors have been devised to facilitate use of retractors. Most of such devices are complicated and expensive, and require some training before they can be used with any speed or skill. Moreover, they can easily be damaged and are difficult to clean and sterilize, due to their many complex components. Of even more concern is that they usually require the use of both of the surgeon's hands or those of his assistant to put them in place and to adjust their retractor components. Their retractors can easily pivot if not tightly secured in place. Such pivoting can change the retracted field so that such devices can actually impede the course of the operation, and may require frequent adjustment.

Accordingly, there is a need for a surgical retractor device that can be rapidly manipulated and adjusted with one hand, is simple in construction, durable and inexpensive, and can be easily cleaned, sterilized and reused. Moreover, the retractors used in such a device should be capable of holding their angle of retraction, i.e., they should not pivot or permit undesired shifting or change in the retracted field. Yet they should be easily repositionable with one hand as needed from time to time throughout the operation.

SUMMARY OF THE INVENTION

The foregoing needs have been satisfied by the improved surgical retractor device of the present invention. The device is substantially as set forth in the Abstract above. Thus, a preferably flat, ring-shaped retractor frame is provided to which a plurality of retractors are releasably but non-pivotably secured so that their depending retraction-effecting ends are positioned in the central work space defined by the frame. The frame may be curved (e.g. bowed or a spherical section) if desired. The retractors can easily be placed on the frame and repositioned as desired, all with one hand, due to a unique arrangement of connectors in the form of mating protrusions or studs and recesses or holes in the frame and retractors. Preferably, the retractor holes have narrowed portions which lock the retractors to the frame against movement except in one direction. In any event, each retractor is connected to the frame at two spaced points so that pivoting of the retractor relative to the frame is prevented.

The device need not have any moving parts. Only the studs and holes interrupt the surfaces of the frame and retractors. Consequently, the device is easy to manufacture, clean, sterilize, use and reuse. It requires no training period and cannot be used incorrectly. It saves time and confusion in the operating room, since it can be so easily manipulated by a single hand. Other features of the invention are set forth in the following detailed description and accompanying drawings.

BRIEF DESCRIPTION OF THE DRAWINGS

A better understanding of the invention may be had from a consideration of the following detailed description, taken in conjunction with the accompanying drawings, in which:

FIG. 6 is a schematic fragmentary perspective view of the device of said first embodiment, with the retractors of FIGS. 2 and 3 in place on the frame of FIG. 1;

FIG. 7 is a schematic top plan view of a third preferred embodiment of the frame used in the device of the invention; and FIG. 8 is a schematic bottom plan view of a retractor used with the frame of FIG. 7.

DESCRIPTION OF THE PREFERRED EMBODIMENTS

FIGS. 1, 2, 3 and 6

Figure 1:
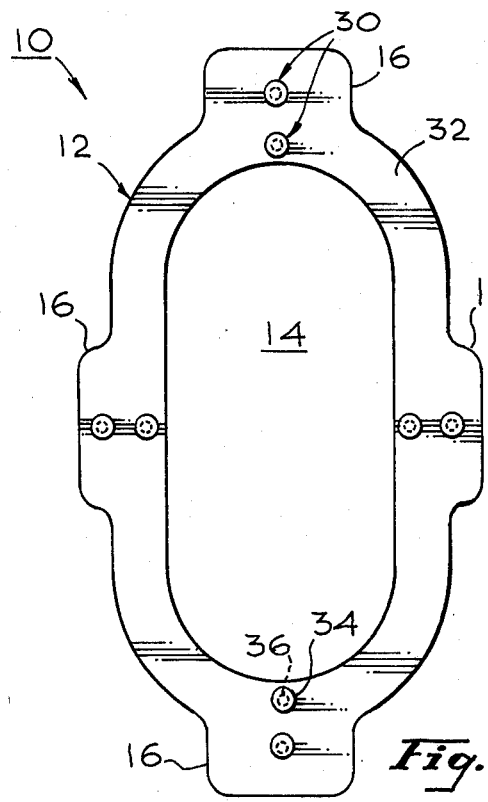
FIG. 1 is a schematic top plan view of a first preferred embodiment of the frame of the improved surgical retractor device of the invention.

Now referring more particularly to FIG. 6 of the drawings, a first embodiment of the improved surgical retractor device of the invention is set forth schematically in fragmentary perspective view. As shown in FIG. 6, a retractor device 10 is provided which comprises a retractor frame 12 which is generally flat, thin, and ring-shaped (FIG. 1) and has an open central working portion 14 defined thereby. Frame 12 is provided with a plurality (4) of support shelves 16, spaced 90° from each other at points along frame 12. A plurality of retractors 18 (FIG. 2) and 19 (FIG. 3) are releasably secured to shelves 16. Each retractor 18 and 19 comprises an elongated, generally flat, thin arm 20 with a depending end 22. In each retractor 18, end 22 is in the form of a smoothly-curved dished wall 24, while in each retractor 19, end 22 is in the form of a fork 26 with spaced tines 28. Wall 24 and fork 26 are adapted to retract tissue when the latter is in a surgical field disposed within central portion 14 of frame and retractors 18 and 19 are positioned as shown in FIG. 6, with walls 24 and forks 26 in partition 14.

Connectors are provided to releasably engage retractors 18 and 19 with frame 12, as shown in FIG. 6. Such connectors comprise, in part, a plurality (in this instance two) of protrusions 30 extending in a line up from the top surface 32 of frame 12 in the area of each of the shelves 16 as shown in FIG. 1. Each pair of protrusions 30 is aligned 90° from each of the adjacent pairs of protrusions 30. Protrusions 30 are each in the form of a stud having an enlarged head 34 and a narrowed neck portion 36.

Figure 2:
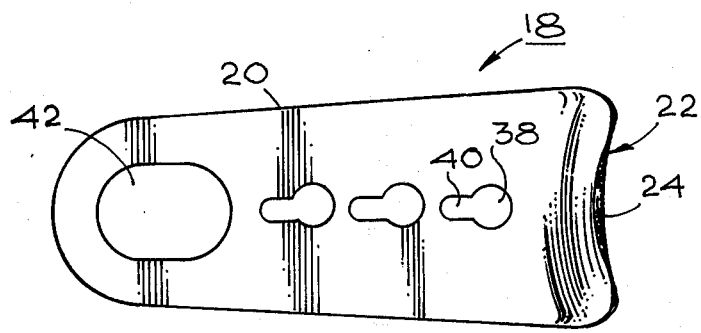
FIG. 2 is a bottom plan view of a first retractor utilized with the frame of FIG. 1.
Figure 3:
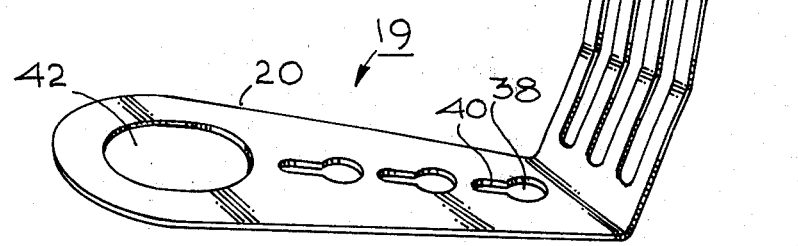
FIG. 3 is a schematic perspective view of a second retractor utilized with the frame of FIG. 1.

The connectors also comprise recesses in the form of holes 38 in retractor arms 20 which mate with protrusions 30. A plurality of holes 38 (in this instance three) are provided in a line through each arm 20 and along its length, as shown in FIGS. 2, 3 and 6. Holes 38 are large enough to receive heads 34 therethrough. Each hole 38 has a narrowed portion 40 positioned on the side of hole 38 farthest away from end 22 of retractor 18 or 19. Portion 40 is dimensioned to receive neck 36 of the protrusion 30 but not head 34. Accordingly, portion 40, when engaged with neck 36, prevents retractor 18 or 19 from moving in any direction except one, and that is away from central portion 14 directly along the line of holes 38 through which retractor 18 or 19 engages frame 12.

Device 10 is used by placing frame 12 (with protrusions 30 facing up) over the surgical field. Retractor 18 or 19 can be engaged with frame 12 at any shelf 16 by merely aligning with one hand the holes 38 and heads 34, while keeping end 22 pointed toward central portion 14 and engaging the tissue to be retracted, then passing holes 38 down over aligned heads 36 and sliding retractor 18 or 19 toward portion 14 until necks 36 are locked in portions 40. Normally, the elastic tissue retracted by end 22 will pull or slide arm 20 into the desired locked position. Once heads 34 and holes 38 are engaged, retractor 18 or 19 cannot be pivoted out of alignment, and once necks 36 and portions 40 are engaged, no sideways movement of the retractor is possible. This is a great advantage, since it assures that the tissue being retracted will remain retracted exactly as desired. No tissue slippage or shape change in the surgical field can occur.

However, when it is desired to remove the retractor 18 or 19, or to change its position, this can easily be done by sliding the retractor with one hand (as by a finger through a finger hole 42 in the distal end of arm 20) away from central portion 14 enough to disengage necks 36 and portions 40 and then lifting arm 20 up to clear holes 38 from heads 36, then disengaging end 22 from the retracted tissue or, if repositioning of arm 20 and reengaging holes 38 on heads 36 is desired, this can be done, as previously described for the initial engagement. For the purpose of permitting such multiple repositioning of arm 20, a greater number of holes 38 are provided in arm 20 than heads 36 in each shelf 16.

It will be noted that retractors 18 and 19 and frame 12 are very simple and inexpensive in construction, do not contain hidden recesses, hinges, etc., and so are easy to clean, sterilize, maintain and use. Moreover, they are compact, light in weight and of attractive appearance. Of most importance, they function well, smoothly, rapidly, and provide sure, positive, non-slipping tissue retraction. Frame 12 and retractors 18 and 19 can be made of any suitable, easily-cleanable durable material such as steel, chrome steel, stainless steel, aluminum or other metals, or heavy duty plastic or the like.

Figure 4:
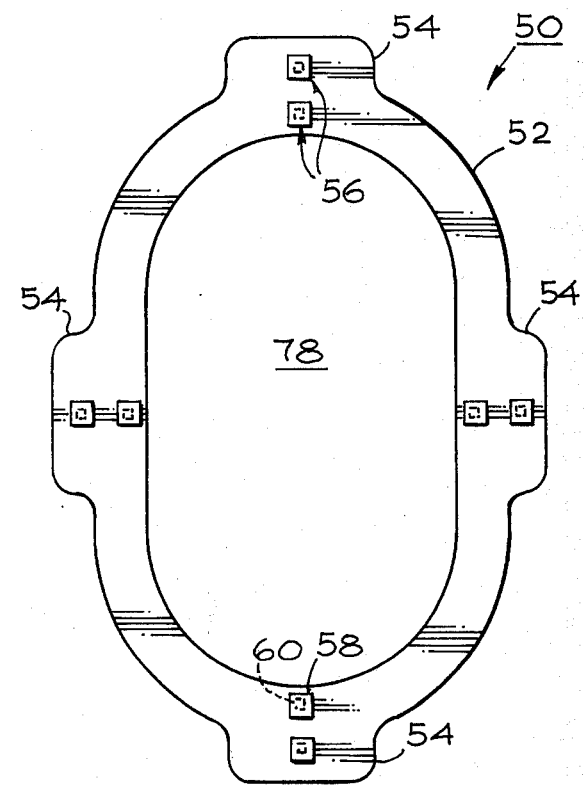
FIG. 4 is a schematic top plan view of a second preferred embodiment of a retractor frame used in the improved surgical retractor device of the invention.
Figure 5:
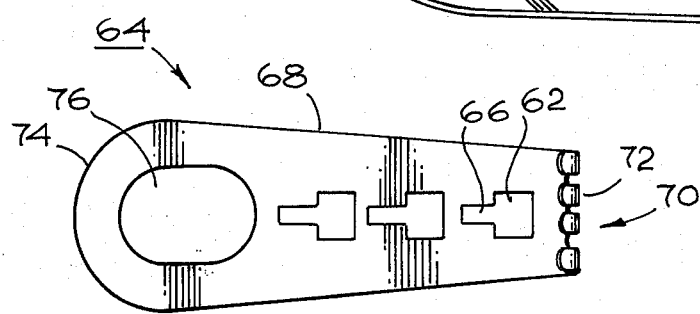
FIG. 5 is a bottom plan view of a retractor for use with the frame of FIG. 4.

FIGS. 4 and 5

A second preferred embodiment of the improved surgical retractor device of the invention is set forth schematically in FIGS. 4 and 5. Thus, a device 50 is shown which comprises a ring-like frame 52 having a plurality of spaced shelves 54, upon each of which are a pair of aligned spaced square stods 56. Each stud 56 comprises an enlarged head 58 and a narrow neck 60. Head 58 is adapted to be received in a square-shaped hole 62 in a retractor 64 (FIG. 5) Neck 60 is adapted to be engaged in a narrow portion 66 of hole 62. Retractor 64 includes a flat elongated arm 68 in which a plurality of holes 62 are longitudinally aligned (FIG. 5), and a depending end 70 containing a tined fork 72 tissue-retracting means and an opposite end 74 containing a finger hole 76 to aid in manipulating retractor 64.

Studs 56 are aligned, as shown in FIG. 4, so that when holes 62 are engaged with heads 58 and necks 60 with portions 66 exactly in the manner described above for device 10, each fork 72 extends into a central surgical field-defining portion 78 of frame 52 for tissue engagement and retraction as described for device 10. The uses, properties and advantages for device 50 are the same as for device 10. Both devices are highly useful and adaptable and fulfill a long-felt need. Device 50 can be made of the same as or different materials from device 10, so long as such materials are durable.

FIGS. 7 and 8

It will be understood that the multiple points of connection between the frame of the device and each retractor, which are necessary to prevent the retractor from pivoting, need not be in a line along the length of the retractor but can be, for example, in side-by-side relation or in a staggered line. One such arrangement is shown schematically in FIGS. 7 and 8, wherein an improved surgical retractor device 90 is depicted. Thus, FIG. 7 shows in top plan view a rectangular open-centered flat frame 92 of device 90, which frame includes openings 94 disposed therethrough in spaced pairs, the openings 94 of each pair being in side-by-side alignment and each pair being disposed at 90° from each adjacent pair around frame 92. Each opening 92 is wedge shaped, with the apex of the wedge directed towards the open center 96 of the frame 92.

Device 90 also includes one or more retractors 98 (FIG. 5), each of which is flat, with an elongated arm 100 and a finger opening 102 at one end 104 and a depending opposite end 106 containing retractor means in the form of a curved wall 108 (FIG. 8) or the like. A pair of wedge-shaped projections 110 aligned in side-by-side spaced relation on and depending from the underside of arm 100 are disposed with the apex of each wedge directed toward end 106. Projections 110 are slightly smaller than openings 94 and are adapted to fit therein to releasably secure each retractor 98 to frame 92. When projections 110 are in openings 94 at a given position on frame 92, end 106 with wall 108 extends into open center 96. When retractor 98 is in the described position and is urged toward center 96 by the elastic tension of tissue engaged with wall 108, each projection 110 is pulled toward the apex of opening 94, wedging it tightly in place and preventing any pivoting of retractor 98 and, in fact, any movement of retractor 98. Accordingly, device 90 has the uses and advantages of devices 10 and 50.

It will be understood that the retractors used in the present devices can be made to intersect the frame thereof at any desired angle, merely by arranging the positioning of the connectors. Various other changes, alterations, modifications and additions can be made in the present device, its components and their parameters. All such changes, alterations, modifications and additions as are within the scope of the appended claims form part of the present invention.

What is claimed is:

1. An improved surgical retractor device, said device consisting essentially of, in combination:
   a. a surgical retractor frame defining an open central work portion with a plurality of retractor positions thereabout;
   b. a plurality of surgical retractors, each retractor comprising an elongated arm with one end depending therefrom and adapted to engage the side of a surgical opening for retraction thereof; and c. a plurality of connector means in the form of at least two spaced frame protrusions and three mating retractor openings per retractor position, the openings being shaped to define a retaining portion remote from the central work portion of the frame and a releasing portion adjacent said central work portion, each retractor being slidable between retaining and releasing positions of the openings relative to the corresponding protrusions to permit changing the operative position of the retractor relative to the central work portion.

2. The improved retractor device of claim 1 wherein each of said arms extends across said frame and wherein each of said depending ends is disposed in said central portion.

3. The improved retractor device of claim 2 wherein said frame is generally flat and generally ring-shaped and wherein said arms are also generally flat.

4. The improved retractor device of claim 3 wherein said connector means includes means for locking with one hand each said retractor against movement in all directions except one.

5. The improved retractor device of claim 3 wherein each said protrusion comprises a stud having an enlarged head and narrowed neck and wherein each said opening comprises a hole into which said head passes.

6. The improved retractor device of claim 5 wherein each said hole includes a narrowed area smaller than said head and adapted to receive said neck for locking said arm in place.

7. The improved retractor device of claim 6 wherein said studs are disposed on said ring and extend generally perpendicular to the main plane of said ring, and wherein said holes extend through said arms and are generally keyhole shaped, said retractors being readily securable to and releasable from said frame with one hand during use of the frame.

8. The improved retractor device of claim 7 wherein at least two of said holes are spaced in each arm along the length thereof with each said narrowed area extending away from said depending end of said retractor.

9. The improved retractor device of claim 7 wherein a sufficient number of said holes are disposed on each said arm to permit each adjustment of the locked position of said depending end relative to said central work portion.

* * * * *